United States Patent [19]
Zeikus et al.

[11] Patent Number: 4,604,352
[45] Date of Patent: Aug. 5, 1986

[54] CO-CULTURE PRODUCTION OF THERMOSTABLE ENZYMERS AND ETHANOL

[75] Inventors: Joseph G. Zeikus, Okemos, Mich.; Hyung-Hwan Hyun, Madison, Wis.

[73] Assignee: Michigan Biotechnology Institute, East Lansing, Mich.

[21] Appl. No.: 652,588

[22] Filed: Sep. 18, 1984

[51] Int. Cl.$^4$ .................... C12D 39/00; C12D 7/14; C12N 9/34; C12N 9/44
[52] U.S. Cl. .................................. 435/42; 435/162; 435/205; 435/210; 435/842
[58] Field of Search ............... 435/42, 161, 162, 163, 435/165, 253, 205, 200, 210, 842

[56] References Cited

PUBLICATIONS

Zeikus, J. G., A. Ben-Bassat, and P. Hegge. 1980, Microbiology of Methanogenesis in Thermal, Volcanic Environments, J. Bact. 143: 432–440.
Schink, B., and J. G. Zeikus, 1983, Clostridium thermosulfurogenes sp. nov., A New Thermophile That Produces Elemental Sulfur From Thiosulphate. J. Gen. Microbiol. 129: 1149–1158.
Hyun, H. H., J. G. Zeikus, R. Longin, J. Millet, and A. Ryter, 1983, Ultrastructure and Extreme Heat Resistance of Spores from Thermophilic Clostridia, J. Bact. 156: 1332–1337.
Matteuzzi, D., F. Hollaus, and B. Biavati, 1978, Proposal of neotype for Clostridium thermohydrosulfuricum and the merging of Clostridium tartarivorum with Clostridium thermosaccharolyticum. Int. J. System, Bacteriol, 28: 528–531.
Lovitt, R. W., R. Longin and J. G. Zeikus, 1984, Ethanol Production by Thermophilic Bacteria: Physiological Comparison of Solvent Effects on parent and alcohol-tolerant strains of Clostridium thermohydrosulfuricum, Appl. Environ. Microbiol, 48: 171–177.
Zeikus, J. G. 1983, Metabolic Communication Between Biodegradative Populations in Nature, In: Microbs in their natural environments, J. H. Slater, R. Whittenbury and J. W. T. Wimpenny (Eds.) Symposium 34 Society for General Microbiology Ltd. Cambridge University Press 1983.
Zeikus, J. G. and T. K. Ng. 1982, Thermophilic Saccharide Fermentations In: Annual Report of Fermentation Processes. G. Tsao, Editor, vol. 5, 7: 263–289.
Ng. T. K., A. Ben–Bassat, and J. G. Zeikus, 1981, Ethanol Production by Thermophilic Bacteria: Fermentation of Cellulosic Substrates by co-cultures of Clostridium thermocellum and Clostridium thermohydrosulfuricum Appl. Environ. Microbiol. 41: 1337–1343.
Zeikus, J. G. 1979, Thermophilic Bacteria: Ecology, Physiology, and technology, Enzyme Microb. Technol. 1: 243–252.

Primary Examiner—Thomas G. Wiseman
Assistant Examiner—Rebecca L. Thompson
Attorney, Agent, or Firm—Quarles & Brady

[57] ABSTRACT

Starch is converted directly to ethanol by growing a co-culture of Clostridium thermosulfurogenes and Clostridium thermohydrosulfuricum under anaerobic conditions on a starch containing substrate in a medium comprising essential vitamins, minerals and growth factors. The co-culture also produces the thermostable enzymes β-amylase, glucoamylase and pullulanase.

4 Claims, 7 Drawing Figures

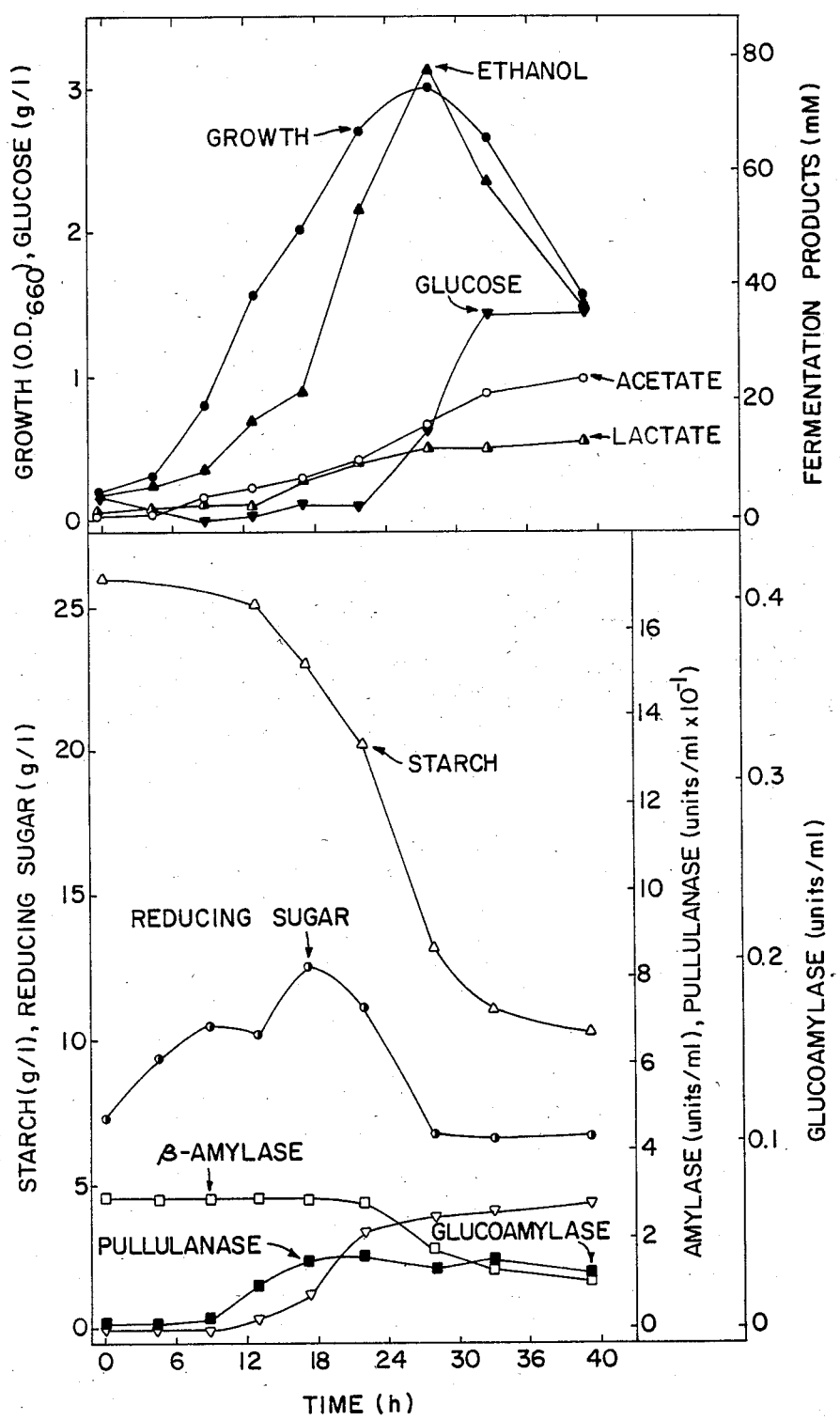

CO-CULTURE PRODUCTION OF THERMOSTABLE ENZYMERS AND ETHANOL

FIELD OF THE INVENTION

The present invention relates to the production of enzymes. More particularly, it relates to the production of thermostable enzymes and ethanol by co-cultures of microorganisms.

BACKGROUND OF THE INVENTION

There is an active interest in the production of industrial feedstock chemicals or fuels from biomass. Starch is a major component of agricultural crops and of corn processing waste and it is a preferred substrate for chemical and enzyme production because of its chemical composition and its higher density than other forms of biomass which facilitates prolonged storage, and decreases transportation and pretreatment costs.

Starch is known to be a valuable starting material for the enzymatic production of sugar, such as glucose, which may be converted by yeast to ethanol. The main amylolytic or starch converting enzymes used for the industrial production of glucose, maltose and maltosaccharide from starch are α-amylase, β-amylase, glucoamylase and pullulanase.

The known amylolytic enzymes, except for bacterial α-amylases, are unstable at the elevated temperatures preferred for the industrial conversion of starch.

It would be desirable to have both a method for the direct bioconversion of starch into ethanol and production of thermostable starch converting enzymes which could be used at the elevated temperature preferred by industry.

BRIEF SUMMARY OF THE INVENTION

The primary objects of the present invention are to disclose a method for directly converting starch to ethanol and to disclose thermostable starch converting enzymes.

It is a further object to disclose a novel co-culture of microorganisms which can co-produce ethanol directly from starch and also produce thermostable starch converting enzymes.

We have discovered a simultaneous, enhanced, single step method for the production of both ethanol and thermostable starch converting enzymes which comprises culturing a co-culture of Clostridium thermosulfurogenes and Clostridium thermohydrosulfuricum under anaerobic conditions on a growth medium containing starch and essential minerals, vitamins and growth factors until detectable enzymatic activity and/or ethanol are present and then, if desired, isolating the enzymes and/or ethanol.

The thermostable starch converting enzymes produced by the co-culture are a β-amylase produced by C. thermosulfurogenes and a pullulanase and a glucoamylase produced by C. thermohydrosulfuricum.

The foregoing and other advantages and objects are accomplished by the present invention which is further described in the drawings and the description of the preferred embodiment.

BRIEF DESCRIPTION OF THE DRAWINGS

FIG. 7. Shows the starch fermentation time when grown in the presence of added β-amylase from C. thermosulfurogenes at pH 7.0 under conditions of continuous gassing.

DESCRIPTION OF PREFERRED EMBODIMENT

Figure 1:
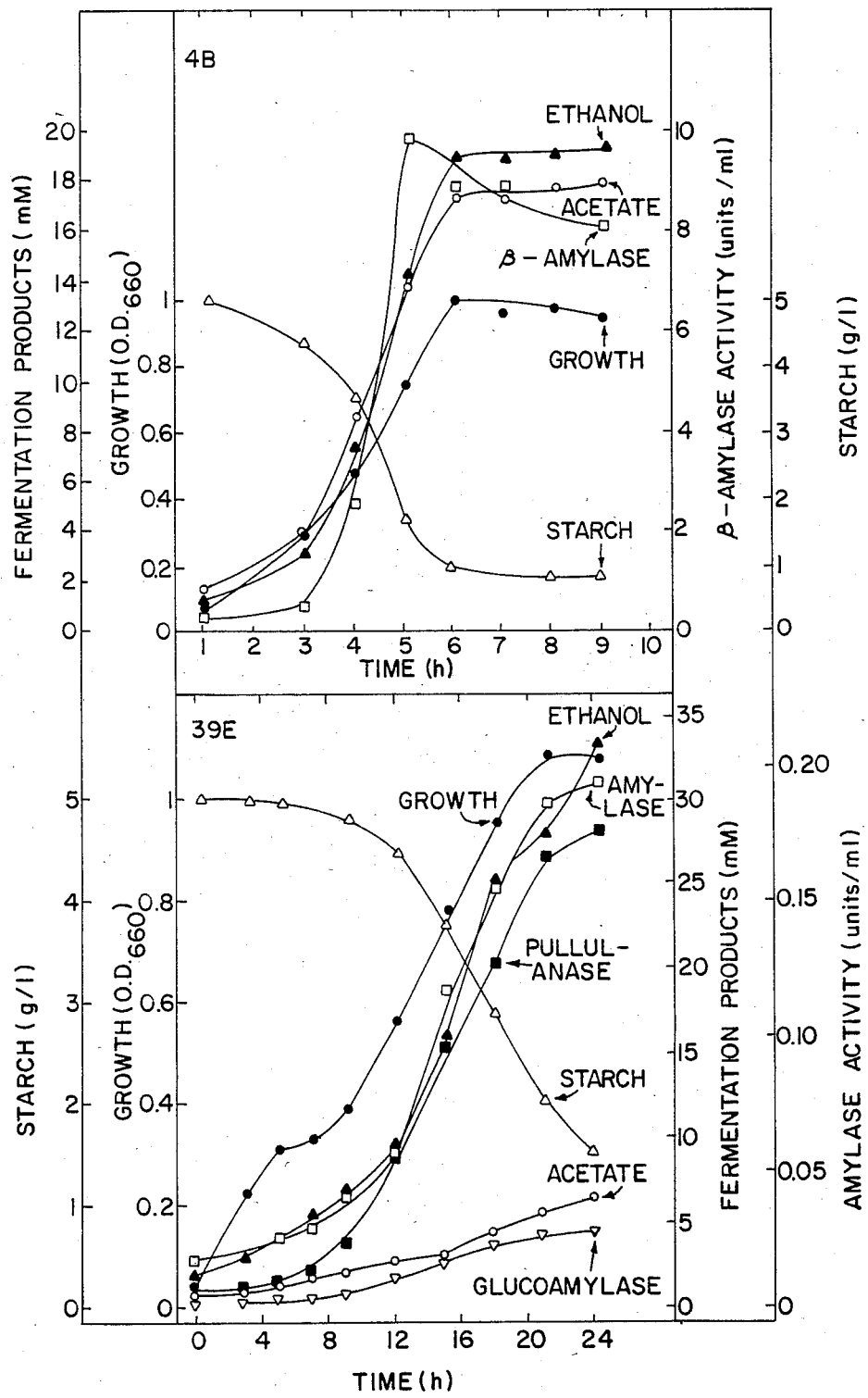
FIG. 1. Shows the starch fermentation time courses of C. thermosulfurogenes 4B and C. thermohydrosulfuricum 39E. The experiments were conducted in sealed Erlenmeyer flasks that contained 400 ml of TYE medium with 0.5% soluble starch, and, which were incubated without shaking at 60° C. for C. thermosulfurogenes and 65° C. for C. thermohydrosulfuricum.

In the preferred practice of the present invention, the co-culture of C. thermosulfurogenes and C. thermohydrosulfuricum is grown under anaerobic conditions at about 60° C. on a substrate of starch in a medium comprising a source of assimilable nitrogen, essential vitamins and minerals and growth factors until detectable enzymatic activity or ethanol is present and then, if desired, isolating the enzymes and/or ethanol. The enzymes produced are a thermostable β-amylase, a thermostable glucoamylase and a thermostable pullulanase.

Materials and Methods

Chemicals and gases.

All chemicals were reagent grade an obained from either Malinckrodt (Paris, KY., U.S.A.) or Sigma (St. Louis, MO., U.S.A.). The $N_2/CO_2$ (95:5) gas was obtained from Matheson (Joilet, IL., U.S.A.), and purified free of oxygen by passage over the heated (370° C.) cop fillings.

Organisms and growth conditions.

C. thermohydrosulfuricum strain 39E ATCC 33223 (1) and C. thermosulfurogenes strain 4B ATCC 33743 (2) were isolated from Octopus Spring in Yellowstone National Park. Anaerobic culture techniques (1) were employed for media preparation and cell cultivation. *C. thermohydrosulfuricum* and *C. thermosulfurogenes* were routinely grown at 65° C. and 60° C., respectively, in 26-ml anaerobic pressure tubes (Bellco Glass Co., Vineland, N.J., U.S.A.) that contained 10 ml of TYE medium (4) with 0.5% glucose or soluble starch, and a $N_2/CO_2$ (95:5) gas head space. Culture media were autoclaved for 45 min to assure destruction of the extremely heat resistant spores of thermoanaerobes (3). For starch metabolism studies in anaerobic pressure tubes and small fermentors, TYE medium was modified to contain the double strengths of vitamin solution, ammonium chloride, magnesium chloride and trace mineral solution. In co-culture studies on 5% starch in a large fermentor, TYE medium was modified to contain 4 times the vitamin solution, magnesium chloride and trace mineral solution, and 2 times ammonium chloride.

Co-cultures and mono-cultures of *C. thermosulfurogenes* were incubated at 60° C., and mono-cultures of *C. thermohydrosulfuricum* at 65° C., throughout this study. A 5% inoculum was applied for all mono-cultures. Co-culture experiments were initiated by injection of a 2.5% inoculum of each organism which were separately grown until the late logarithmic growth phase. The inoculum was prepared in sealed vessels that contain the same medium as in the experiments.

Starch metabolism time course studies on 2.5% starch were conducted in a small New Brunswick Multigen fermentor (New Brunswick Scientific Co., Edison, N.J.) that contained 650 ml of the modified TYE medium. The fermentors were mixed at 200 pm, gassed continuously with $N_2/CO_2$ (95:5) at a flow rate of about 0.4 VVM, and pH-controlled with 1.7N ammonium hydroxide solution.

Starch metabolism time course studies of co-cultures on 5% starch were conducted in a large 14-liter New Brunswick Microfermentor that contained 8 liters of the modified TYE medium. For ethanol recovery, 2 Erlenmeyer flasks (6-liter) that contained 4 liters of water each, respectively, were connected to the fermentor in tandum and were kept in ice baths during the fermentation period. A condensor was connected to the fermentor and the condensate was displaced into the first flask. The gas flow rate was 0.056 VVM.

In mono-culture studies of *C. thermohydrosulfuricum* with β-amylase of *C. thermosulfurogenes*, the enzyme was injected (3 units/ml) after sterilization by membrane filtration. The β-amylase was prepared from a *C. thermosulfurogenes* culture which was grown in a 14-liter fermentor containing 10 liters of LPBB medium (4) with 1% maltose and 0.02% yeast extract. The culture supernatant was obtained with a Dupont (Wilmington, DE.) KSB continuous-flow centrifuge system and was concentrated (5).

Quantification of growth, substrates, and products.

Culture turbidities were determined by inserting anaerobic pressure tubes into a Spectronic 20 spectrophotometer (Bausch and Lomb, Rochester, N.Y.). In all growth experiments, except for anaerobic pressure tube cultures, culture broths were diluted 5 times with double distilled water to measure optical density. To measure starch concentration, the culture broth samples were appropriately diluted with water and 50 ml of sulfuric acid solution (5M) was added to 0.5 ml samples. These samples were placed in steam bath for 3 hours and then neutralized by the addition of 35 μl sodium hydroxide solution (10N). The reducing sugar content was measured by the dinitrosalicylic acid method. Starch concentration was estimated by fitting the reducing sugar values to the calibration curve for starch solutions which were treated by the same procedures as above.

Glucose was enzymatically determined by the hexokimase and glucose-6-phosphate dehydrogenase method. Reducing sugar was estimated using glucose as a standard by the dinitrosalicylic acid method. Total carbohydrate was assayed by the phenol-sulfuric acid method.

The ammonium content of the culture fluid was measured by known procedures and ethanol and acetate were measured by gas chromatography using a flame ionization detector (4). L-Lactic acid was assayed by standard procedures using lactic dehydrogenase. Hydrogen was quantified by thermal conductivity detection (6) procedures. $CO_2$ production was calculated by the sum of ethanol and acetate production.

Enzyme assays.

Cell-free culture broth and washed cell suspensions were used for measurements of β-amylase and other amylolytic enzyme activities, respectively. They were prepared by centrifugation of culture broths at 10,000×g for 10 min to separate the cells and culture broth. The precipitated cells were suspended in the appropriate amount of double distilled water.

Amylase or β-amylase activity was assayed by measurement of reducing power which was liberated during reaction on starch. The reaction mixture (5 ml) consisted of 2% soluble starch in 0.1M sodium acetate buffer (pH 6.0) and the appropriately diluted enzyme. After aerobic incubation at 60° C. for 30 min, the reaction was stopped by cooling on ice. The released reducing sugar was measured by the dinitrosalicylic acid method.

Pullulanase activity was assayed by analyzing the reducing power released from pullulan, using the dinitrosalicylic acid method. The reaction mixture consisted of 0.5 ml of 2% pullulan in 0.2M phosphate buffer (pH 7.0) and 0.5 ml of enzyme solution. The reaction was performed at 60° C. for 30 min., and was stopped by cooling on ice and adding 4 ml of cold dinitrosalicylic acid solution. One unit of amylase, β-amylase or pullulanase is defined as the amount of enzyme which liberated 1 μmol of reducing sugar as a glucose standard per min under the described conditions.

Glucoamylase activity was measured after incubating the reaction at 60° C. for 30 min. The reaction mixture consisted of 0.5 ml of 2% soluble starch solution in 0.2M sodium acetate buffer (pH 4.8) and 0.5 ml of enzyme solution. The reaction was stopped by cooling on ice, and then it was boiled in a steam bath for 10 min. The released glucose was quantified using the hexokinase and glucose-6-phosphate dehydrogenase method. One unit of glucoamylase is defined as the amount of enzyme that liberated one μmole of glucose per min under the conditions.

Results

Starch metabolism by Monocultures.

FIG. 1 compares starch transformation time courses for *C. thermohydrosulfuricum* and *C. thermosulfurogenes* when they were cultured in complex medium without shaking and pH-control. For both species, the synthesis of amylolytic enzymes (i.e., β-amylase, glucoamylase and pullulanase) was closely related to growth and hence these amylases are produced as primary metabolites. Under these experimental conditions, starch was not completely utilized by either species during the time course.

The incomplete utilization of starch by *C. thermohydrosulfuricum* appears related to growth inhibition caused by high hydrogen or proton production (7) because pullulanase and glucoamylase activity completely hydrolyze starch. In contrast, the inability of *C. thermosulfurogenes* to completely utilize starch was a function the accumulation of limit dextrins caused by the absence of pullulanase or a debranching activity (5).

ture. The dextrose equivalent (DE) values of the remaining carbohydrates were about 74 in co-culture versus 39 in mono-cultures. Therefore, the cessation of growth before complete utilization of the accumulated saccharides is suggested to be due to the accumulation of toxic hydrogen (for 39E) or protons (for both strains). The final ethanol concentrations achieved here are not inhibitory to growth of either *C. thermohydrosulfuricum* (8) or *C. thermosulfurogenes*.

TABLE 1

Comparison of Starch Metabolism Parameters in Mono- and Co-Culture Fermentations of *C. thermohydrosulfuricum* (39E) and *C. thermosulfurogenes* (4B)

| Condition | Culture | Growth ($OD_{660}$) | pH | Starch Remaining (g/l) | Reducing Sugar Remaining (g/l) | Amylase Activities (U/ml culture) | | | Fermentations Products (mol/10 ml culture) | | | | |
|---|---|---|---|---|---|---|---|---|---|---|---|---|---|
| | | | | | | -Amylase | Pullu- lanase | Gluco- amylase | Ethanol | Ace- tate | Lac- tate | $H_2$ | $CO_2$ |
| I. 0.65% Starch | 39E | 1.9 | 6.1 | 0.5 | 0.3 | N.D. | 0.34 | 0.053 | 540 | 100 | 130 | 43 | 640 |
| | 4B | 1.3 | 4.3 | 2.3 | 0.2 | 8.6 | N.D. | 0.009 | 280 | 159 | 66 | 244 | 439 |
| | 39E + 4B | 1.5 | 4.7 | 0.0 | 0.0 | 10.0 | 0.16 | 0.024 | 550 | 151 | 99 | 228 | 701 |
| II. 3.0% Starch | 39E | 2.7 | 6.0 | 22 | 8.7 | N.D. | 0.39 | 0.066 | 910 | 91 | 220 | 34 | 1001 |
| | 4B | 2.7 | 4.3 | 22 | 8.6 | 11.1 | N.D. | 0.009 | 610 | 256 | 234 | 378 | 866 |
| | 39 + 4B | 3.8 | 4.7 | 19 | 14 | 8.7 | 0.35 | 0.052 | 970 | 222 | 288 | 278 | 1192 |

Conditions: 26 ml pressure tubes contained a complex medium with trypticase (1%) and yeast extract (0.3%), a $N_2$—$CO_2$ headspace and were incubated for 36 h at 60° C. without shaking. N.D. means not detectable or less than 0.59 U/ml of amylase activity or 0.001 U/ml pullulanase activity.

Under these conditions, the exponential growth rate in doublings per hour of the two species on starch versus glucose were: 1.5 versus 1.2 for *C. thermosulfurogenes;* and 4.1 versus 1.9 for *C. thermohydrosulfuricum*. The slower growth rate of *C. thermohydrosulfuricum* on starch is considered to be a reflection of limited glucoamylase activity and lack of $\beta$-amylase activity. Neither species produce significant amounts of $\alpha$-amylase activity.

Comparison of starch metabolism by mono- and co-cultures.

Experiments were initiated to test the hypothesis that starch transformation rates would be enhanced in co-culture versus mono-culture fermentation.

Figure 2:
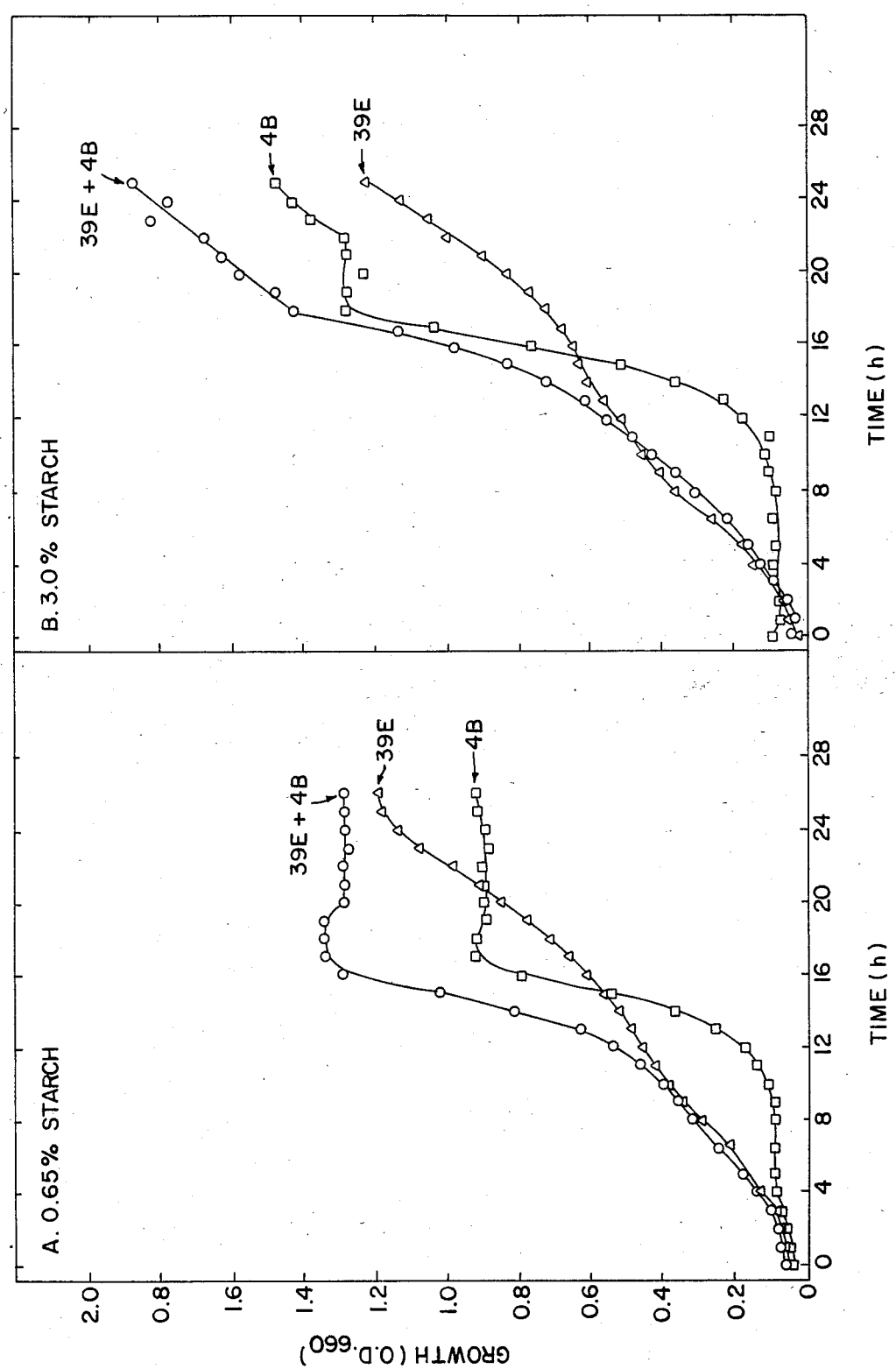
FIG. 2. Shows the mono- and co-culture growth curves of C. thermosulfurogenes 4B and C. thermohydrosulfuricum 39E in complex medium (modified TYE medium) containing 0.65% (A) or 3.0% (B) of soluble starch. The experiments were conducted in pressure tubes that contained 10 ml of TYE medium and which were incubated without shaking at 60° C. for mono- and co-cultures of C. thermosulfurogenes and 65° C. for mono-culture of C. thermohydrosulfuricum.

FIG. 2 compares growth of mono- and co-cultures of these thermo anaerobes on starch in sealed pressure tubes. In mono culture, *C. thermohydrosulfuricum* grew slowly but without a significant lag phase; whereas, *C. thermosulfurogenes* displayed a lag phase but growth was more rapid upon initiation. In co-culture, growth initiated without a lag, and was very rapid in the logarithmic growth phase. Hence, growth rate and total cell concentration in co-culture fermentation was higher than in mono-culture fermentations.

Figure 3:
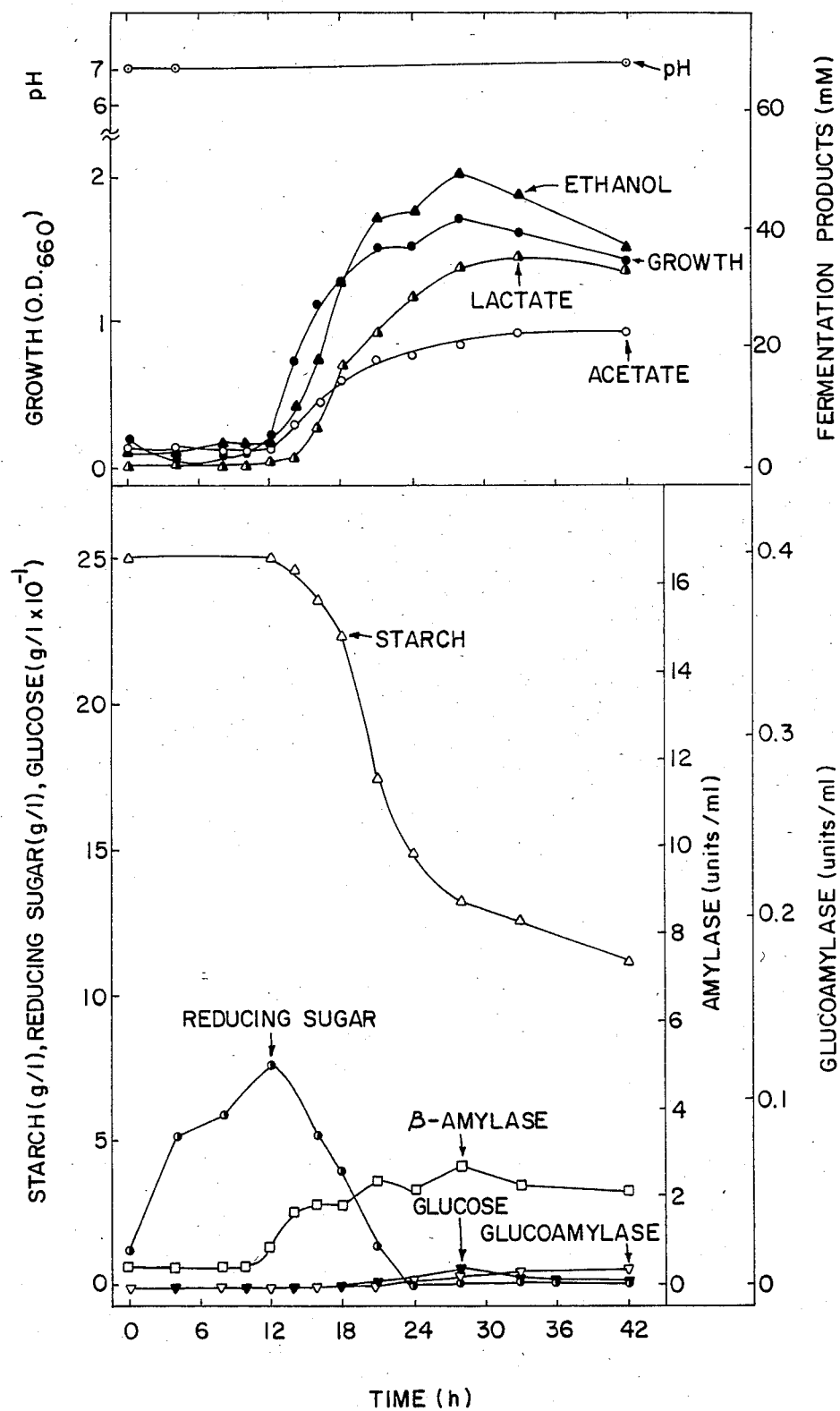
FIG. 3. Shows the mono-culture starch metabolism time course of C. thermosulfurogenes at pH 7.0 in a gassed fermentor. The experiment was conducted in a fermentor that contained 650 ml of the modified TYE medium, 2.5% starch, and, which was gassed with $N_2/CO_2$ (95:5), and incubated at 60° C. with mixing. The mono-culture was initiated by injection of a 5% inoculum grown on the same medium.
Figure 4:
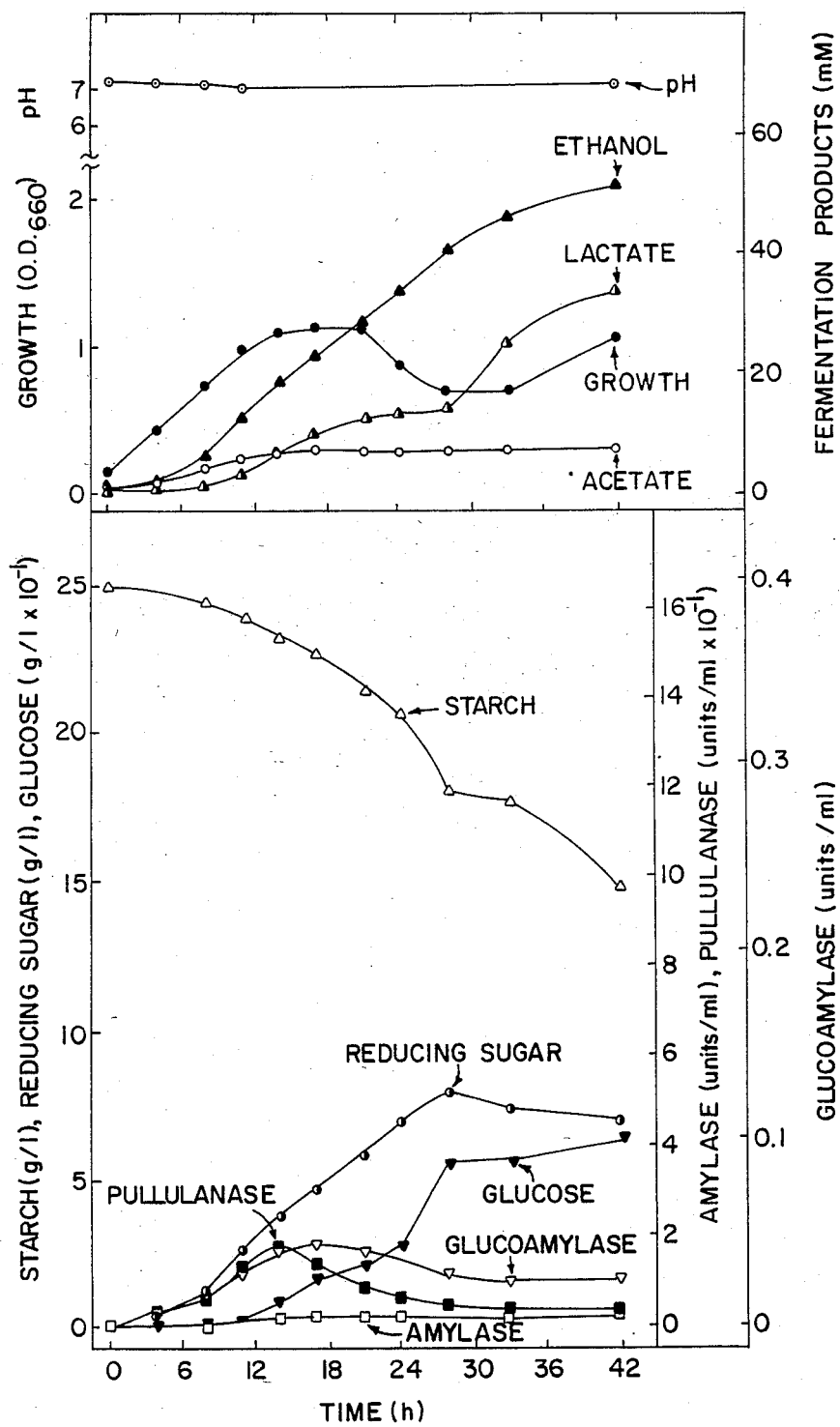
FIG. 4. Shows the mono-culture starch metabolism time course of C. thermohydrosulfuricum at pH 7.0 in a gassed fermentor. The experimental conditions were the same as in FIG. 3, except for inoculum source and incubation at 65° C.
Figure 5:
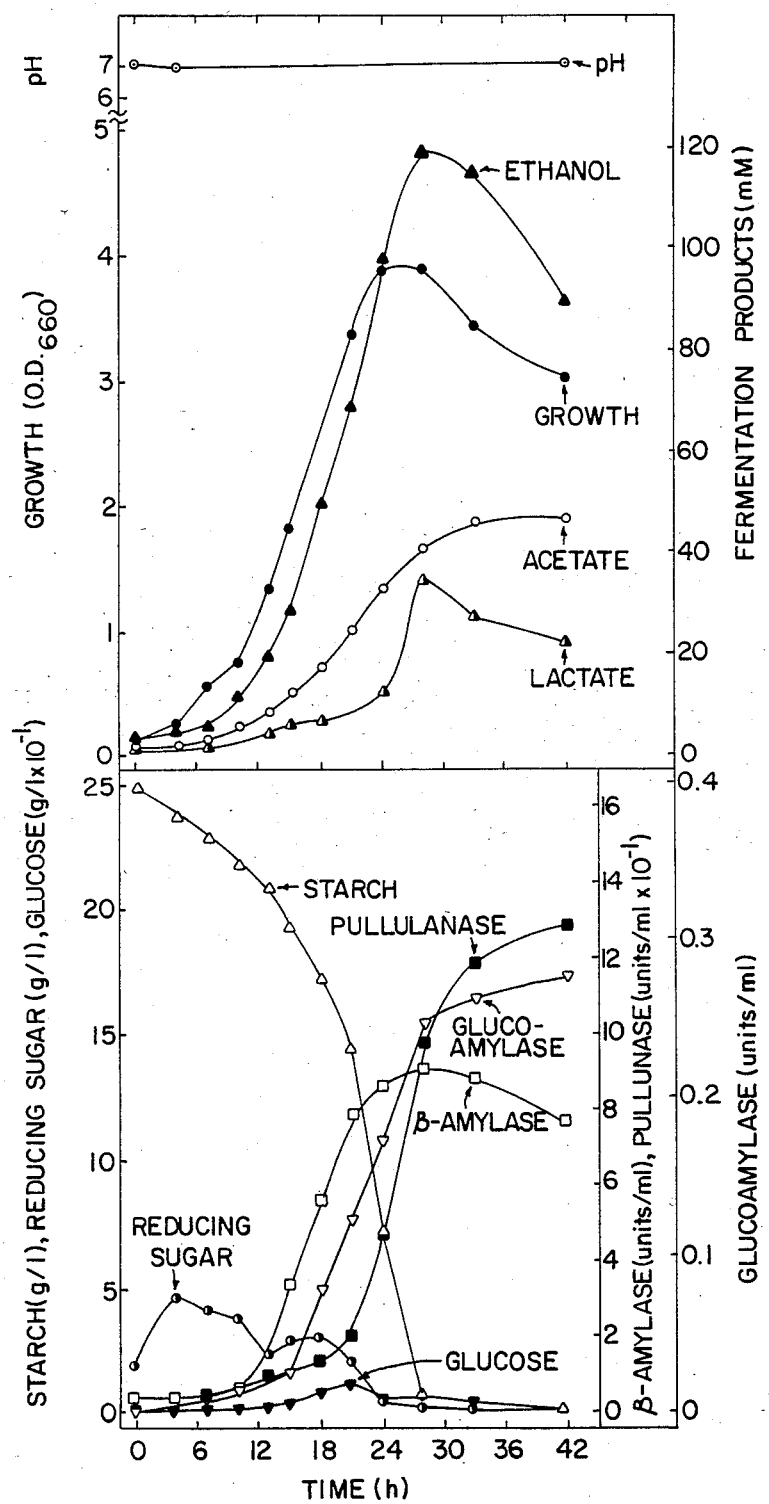
FIG. 5. Shows the co-culture starch metabolism time course of C. thermosulfurogenes and C. thermohydrosulfuricum at pH 7.0 in a gassed fermentor. Co-cultures were initiated by injection of a 2.5% inoculum of each organism. Other conditions were the same as in FIG. 3.

Table 1 compares the starch metabolism parameters of mono- and co-culture fermentations in sealed pressure tubes. Total growth was enhanced by co-culture fermentation at high starch concentrations. Starch was completely utilized by the co-cultures at low but not high starch concentrations. The production of $\beta$-amylase was not significantly different in mono- versus co-cultures of *C. thermosulfurogenes*. It is notable that all three amylases (i.e., $\beta$-amylase, glucoamylase and pullulanase) were simultaneously expressed in co-culture fermentations. The concomitant growth of both species in co-culture was indicated by: the simultaneous production of all three amylolytic activities; enhanced utilization of starch; and higher total levels and ratios of end products. The ratio of reducing sugar accumulation to starch remaining in mono- versus co-cultures at 3% starch indicates a higher conversion of starch into the low molecular weight oligosaccharides by the co-cul- In order to eliminate toxic effects of hydrogen or protons, mono- and co-culture experiments were performed in small fermentors that were pH controlled at 7.0 and continuously gassed with $N_2/CO_2$ (95:5). PH was controlled with ammonium hydroxide solution (1.7M) because preliminary experiments demonstrated that growth was ammonium limited at greater than 1% starch in normal TYE medium. FIGS. 3, 4 and 5 compare mono- and co-culture starch fermentations under these conditions.

FIG. 3 shows the fermentation time course of *C. thermosulfurogenes* grown on 2.5% starch at pH 7.0. The mono-culture displayed an initial lag phase where a high amount of reducing sugars accumulated as a result of active, extracellular $\beta$-amylase action (5). The accumulated reducing sugars were rapidly consumed when growth initiated; and, both $\beta$-amylase production and end product formation occurred simultaneously during the logarithmic growth phase. Starch was incompletely used, however, which implied that the $\beta$-limit dextrins formed by $\beta$-amylase were not further metabolized due to lack of pullulanase activity. The decrease of ethanol concentration observed during the stationary growth phase was the result of evaporation caused by gassing.

A starch metabolism time course of *C. thermohydrosulfuricum* grown under conditions of continuous gassing and pH control at 7.0 is illustrated in FIG. 4. This species displayed an unusual fermentation pattern because biphasic growth was observed, which was indicative of extensive cell lysis. Starch also was not completely utilized by this species under the growth conditions employed. Reducing sugar accumulation increased according to the culture time, probably in response to the amylolytic enzymes produced during growth. In addition, glucose accumulated continuously during the entire culture period. This finding suggests that the rate of glucose production by amylase surpassed the glucose consumption rate of the organism.

Amylase activities were measured in cell free culture broth of *C. thermohydrosulfuricum* in order to determine whether cell lysis occurred during growth. Glucoamylase and pullulanase activities in supernatants were not detected in the early to mid exponential growth phase, but after that, the activities gradually increased. Supernatant glucoamylase and pullulanase activities after cultivation for 42 hours, were 0.22 and 0.27 units/ml, respectively, which implied extensive release of amylases into the culture fluid by cell lysis. This was confirmed by microscopic observation of lysed cells in the culture. Therefore, cell lysis as well as repression of amylase synthesis caused by accumulation of glucose during growth may account for relatively low glucoamylase and pullulanase production by C. thermohydrosulfuricum in mono-culture fermentations.

FIG. 5 shows the dramatic improvement in starch metabolism observed when co-cultures were grown at pH 7.0 under conditions of continuous gassing. Starch was rapidly degraded during the fermentation time course and almost completely consumed at 28 hours. Co-culture fermentations consumed starch more rapidly and completely than mono-cultures grown under similar conditions (see FIG. 3 and FIG. 4). Most importantly, the co-culture produced more cells, total amylases and ethanol. The activities of β-amylase, glucoamylase and pullulanase increased in relation to cell growth. Reducing sugar and glucose accumulation was limited during the co-culture fermentation time course. The co-culture also showed both an enhanced rate and yield of ethanol production. It is interesting to note that after depletion of sugar substrates, lactate was consumed. Balanced growth was achieved by both species in this co-culture as evidenced by: the pattern of growth; complete starch consumption; the simultaneous production of three amylases; and, the ratio of end product formation.

The most remarkable feature of the co-culture fermentation (FIG. 5) was the significant enhancement of glucoamylase and pullulanase production. Growth of both species may have competitively removed low molecular substrates (e.g., glucose) liberated by the coordinate action of amylases, resulting in alleviation of catabolite repression of enzyme synthesis. The amylase synthesis in these two species is repressed by glucose. Also, other substrates with α-1, 6 linkages formed by starch hydrolysis which were not attacked by β-amylase, may have more efficiently induced the synthesis of glucoamylase and pullulanase. The glucoamylase and pullulanase activities in cell free co-culture broth at 42 hours were 0.02 and 0.07 units/ml, respectively. This indicated that lysis of C. thermohydrosulfuricum still occurred in co-culture fermentations but not at such significant levels as in mono-culture fermentations.

Figure 6:
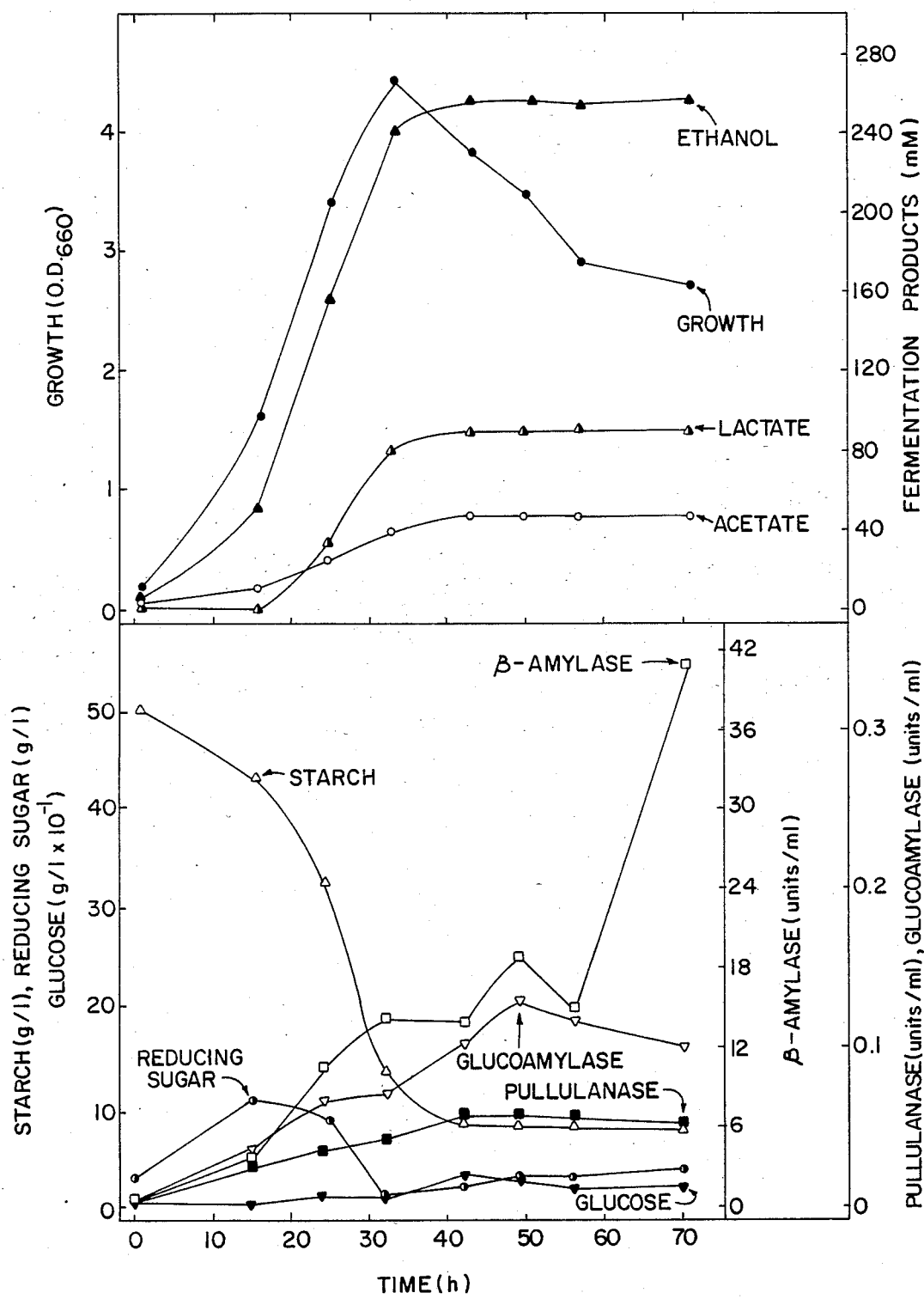
FIG. 6. Shows the co-culture starch metabolism time course of C. thermosulfurogenes and C. thermohydrosulfuricum on on 5% soluble starch at pH 7.0 in a gassed fermentor. The experiment was conducted in a 14 liter fermentor that contained 8 liters of modified TYE medium, and, which was gassed with $N_2/CO_2$ (95:5), and incubated at 60° C. with mixing. A 2.5% inoculum of each organism was used.

FIG. 6 shows the influence of higher starch concentrations (5%) on the fermentation time course of co-cultures grown at pH 7.0, under continuous gassing. This experiment was performed to further improve amylase and ethanol production yield by co-cultures. Under these conditions, starch was rapidly degraded but not completely consumed. End products were formed very rapidly in relation to the high growth rate until high concentrations of ethanol (1.6% v/v) was accumulated. Growth of C. thermohydrosulfuricum (8) and C. thermosulfurogenes wild type strains is inhibited by this concentration of ethanol. Glucose concentration was maintained at fairly low levels during the time course. The final yield of β-amylase but not glucoamylase or pullulanase was enhanced (see FIG. 5). It is notable that β-amylase activity increased very rapidly after the stationary growth phase. The evaporated ethanol removed by gassing the co-culture (FIG. 6) was measured to determine total ethanol produced by in this co-culture fermentation. These results are summarized in Table 2.

About 84% of starch was fermented by the co-culture, and the product yield (i.e., mM ethanol produced per mM glucose as a starch consumed) was 1.7. The maximum specific production rate was 15.0 mmoles of ethanol per g-cell weight per hour.

TABLE 2

Total Soluble End Products Formed by Co-culture Fermentations of C. thermosulfurogenes and C. thermohydrosulfuricum on 5% Soluble Starch Medium

| Starch Consumption (mM as Glucose) | | End Product Formation (mM) | | |
|---|---|---|---|---|
| | | Ethanol | Acetate | Lactate |
| 252 | Fermentor | 265 | 48 | 90 |
| | Reservoir | 19 | | |
| | Total | 284 | | |

The experiment was conducted in a 14 liter fermentor that contained 8 l of modified TYE medium, and, which was gassed with $N_2/CO_2$ (95:5) and incubate with pH control at 60° C. with mixing. Total ethanol values in the reservoir represent those recovered in the off-gas vapors.

Influence of β-amylase on C. thermohydrosulfuricum starch fermentations.

These experiments were performed to verify whether the dramatic improvement of starch metabolism in co-cultures was caused by the coordinate action of amylases alone or by both enzymatic and metaolic cooperations. FIG. 7 shows the starch fermentation time course of C. thermosulfurogenes when grown in the presence of added β-amylase from C. thermosulfurogenes at pH 7.0 under conditions of continuous gassing. Under these conditions, starch was not completely hudrolyzed, similar to mono-cultures (see FIG. 4.). However, growth and end product formation were fairly improved in comparison to the mono-culture of C. thermohydrosulfuricum. Notably, amylase production was not improved. Glucose accumulated in large quantities after the mid logarithmic growth phase and this may have resulted in catabolite repression of glucoamylase and pullulanase synthesis. Therefore, these results imply that improvement of starch metabolism by co-culture fermentation was achieved by the coordinate action of amylolytic enzymes as well as metabolic cooperation between the two species.

Discussion

The forgoing data clearly show that co-culture fermentations comprised of C. thermohydrosulfuricum and C. thermosulfurogenes dramatically enhance the rate and yield of transforming starch into both amylases and ethanol. Furthermore, ethanol and three thermostable amylases-glucoamylase, pullulanase and β-amylase are produced in high yields by a single step fermentation system. In general these findings are of general interest to further understand metabolic interactions in mixed populations of anaerobes (9, 15); and, they are of applied interest for industrial enzyme and ethanol production (10, 11).

The following points summarize the general significance of the results in relation to metabolic regulation and application of amylase activities that were expressed in the co-culture starch fermentation.

1. The rate of starch saccharification was enhanced in co-culture as a consequence of sharing amylase activities to improve rate limiting steps.

2. Total starch saccharification activity was enhanced in co-cultures as key modulators of amylase synthesis (e.g., glucose) were decreased.
3. The total starch metabolism physiology (i.e., growth, enzyme production and fermentation product formation) of the thermoanaerobic species was enhanced in co-culture.
4. The rate and yield of ethanol production from starch was increased in co-culture.
5. Co-culture starch fermentations of these species may have utility in continuous production and recovery of ethanol at high temperature and reduced pressure, or in the production of thermostable amylases for industrial use.

Previously co-cultures (12, 13, 14) have been shown to enhance the yield and rate of a particular fermentation product (e.g. methane or ethanol) formed by two different species of which one lacks the ability to transform a key metabolite (e.g. cellulose or hydrogen). The type of metabolic interaction which explains the present co-culture system is based on the coordinate regulation of different substrate hydrolysing enzymes present in two species. This type of metabolic communication appears to be unique.

The amylolytic enzymes such a $\beta$-amylase, pullulanase and glucoamylase which are needed in starch transformation industries are generally not thermostable at operating conditions used for starch conversion into soluble sugars. Therefore, simultaneous and enhanced production of these thermostable amylases by co-culture starch fermentations provide an inexpensive method for producing industrial amylases needed in both starch saccharification and ethanol production processes. In addition, ethanol can be recovered for its by-product value. The cell bound pullulanase and glucoamylase may be practically applicable for glucose production from starch or maltodextrins; whereas, $\beta$-amylase may be useful for maltose production.

The co-culture fermentation has particular advantages for industrial ethanol production provided the ethanol can be economically removed by continuous reduced pressure distillation. Starch is less expensive than glucose as a feedstock substrate and the co-culture directly produces its own amylase. The utility costs assumed for the co-culture in relation to: not needing aeration; limited mixing; use of metabolic heat; and, the potential to recover ethanol continuously at process temperatures by reduced pressure distillation imply substantial savings. Notably, the productivity rate for starch transformation to ethanol (0.7 g ethanol/g cell/h) is close to the values reported for glucose transformation to ethanol by *Saccharomyces cerevisial* (1 g ethanol/g cell/h). The productivity rate for starch conversion to ethanol by thermoanaerobes should be further enhanced by use of mutants that display higher ethanol tolerance and yield.

References

1. Zeikus, J. G., A. Ben-Bassat, and P. Hegge. 1980. Microbiology of methanogenesis in thermal, volcanic environments. J. Bact. 143: 432–440.
2. Schink, B., and J. G. Zeikus. 1983. *Clostridium thermosulfurogenes* sp. nov., a new thermophile that produces elemental sulphur from thiosulphate. J. Gen. Microbiol. 129: 1149–1158.
3. Hyun, H. H., J. G. Zeikus, R. longin, J. Millet, and A. Ryter. 1983. Ultrastructure and extreme heat resistance of spores from thermophilic Clostridia. J. Bact. 156: 1332–1337.
4. Zeikus, J. G., P. W. Hegge, and M. A. Anderson. 1979. *Thermoanaerobium brockii* gen. nov. and sp. nov., a new chemorganotrophic, caldoactive, anaerobic bacterium. Arch. Microbiol. 121: 41–48.
5. Hyun, H. H., and J. G. Zeikus. 1984. Biochemical Characterization thermostable $\beta$-amylase from *Clostridium thermosulfurogenes* (manuscript submitted).
6. Nelson, D. R., and J. G. Zeikus. 1974. Rapid method for the radioisotropic analysis for gaseous products of anaerobic metabolism. Appl. Environ. Microbiol. 28: 258–261.
7. Matteuzzi, D., F. Hollaus, and B. Biavati. 1978. Proposal of neotype for *Clostridium thermohydrosulfuricum* and the merging of *Clostridium tartarivorum* with *Clostridium thermosaccharolyticum*. Int. J. System. Bacteriol. 28: 528–531.
8. Lovitt, R. W., R. longin, and J. G. Zeikus. 1984. Ethanol production by thermophilic bacteria: physiological comparison of solvent effects on parent and alcohol-tolerant strains of *Clostridium thermohydrosulfuricum*. Appl. Environ. Microbiol. 48: 171–177.
9. Zeikus, J. G. 1983. Metabolic communication between biodegradative populations in nature. In: Microbs in their natural environments. J. H. States, R. Whittenburg and J. W. T. Wimpenny (eds.) Symposium 34 Society for General microbiology Ltd. Cambridge University Press 1983.
10. Zeikus, J. G. and T. K. Ng. 1982. Thermophilic saccharide fermentations In: *Annual report of Fermentation Processes*. 6 TSQO, editor Vol. 5, 7: 263–289.
11. Zeikus, J. G. 1980. Chemical and Fuel Production by anaerobic bacteria. *Annual Review of Microbiology*. 34: 423–64.
12. Ng, T. K., A. Ben-Bassat, and J. G. Zeikus. 1981. Ethanol production by thermophilic bacteria: fermentation of cellulosic substrates by co-cultures of *Clostridium thermocellum* and *Clostridium thermohydrosulfuricum*. Appl. Environ. Microbiol. 41: 1317–1343.
13. Weimer, P. J., and J. G. Zeikus. 1977. Fermentation of cellulose and cellobiose by *Clostridium thermocellum* in presence and absence of *Methanobacterium thermoautotrophicum*. Appl. Environ. Microbiol. 33: 289–297.
14. Wang, D. I. C., F. Biocic, H. Y. Fang, and G. Y. Wang. 1979. Direct microbiological conversion of cellulosic biomass to ethanol, p. 61–67. In proceedings of the 3rd annual biomass energy systems conference, National Technical Information Service, Springfield, Va.
15. Zeikus, J. G. 1979. Thermophilic bacteria: Ecology, physiology, and technology. Enzyme Microb. Technol. 1: 243–251.

The foregoing references are incorporated by reference herein.

It will be apparent to those skilled in the art that a number of modifications and changes may be made without departing from the spirit and scope of the present invention. For example, although in the experimental work the substrate was purified starch other less expensive and more abundant substrates can be used. In addition, pH's and other conditions can be modified within limitations. It will be appreciated by those skilled in the art that the scope of the invention should not be limited to the specific strains of organisms described because genetic variants produced by mutation or genetic recombination techniques and having the enzyme producing capabilities and identifying characteristics of the specifically described organisms can be used. Therefore, the invention is not to be limited except by the claims which follow.

We claim:

1. A method for the co-production of a thermostable β-amylase, a thermostable glucoamylase, a thermostable pullulanase and ethanol which comprises growing a biologically pure co-culture of *Clostridium thermosulfurogenes* and *Clostridium thermohydrosulfuricum* under anaerobic conditions on a carbohydrate substrate in a medium comprising essential vitamins, minerals and growth factors for a time sufficient to produce recoverable amounts of said themostable enzymes and ethanol.

2. A method for the direct conversion of starch to ethanol which comprises growing a biologically pure co-culture of *Clostridium thermosulfurogenes* and *Clostridium thermohydrosulfuricum* under anaerobic conditions on a substrate of carbohydrate in a medium comprising essential vitamins, minerals and growth factors until detectable ethanol is present and then isolating the ethanol that forms.

3. A method for the co-production of a thermostable β-amylase, a thermostable glucoamylase, and a thermostable pullulanase which comprises growing a biologically pure co-culture of *Clostridium thermosulfurogenes* and *Clostridium thermohydrosulfuricum* under anaerobic conditions on a substrate of carbohydrate in a medium comprising essential vitamins, minerals and growth factors until detectable enzymatic activity is present and then isolating the enzymes.

4. A biologically pure co-culture consisting essentially of *Clostridium thermosulfurogenes* and *Clostridium thermohydrosulfuricum* characterized by an ability when cultivated under anaerobic conditions in an aqueous nutrient medium, containing assimilable sources of nitrogen and starch, to directly convert the starch to ethanol and to produce a thermostable β-amylase, a thermostable glucoamylase and a thermostable pullulanase.

* * * * *